United States Patent
Rees et al.

(10) Patent No.: US 6,376,498 B1
(45) Date of Patent: Apr. 23, 2002

(54) PHARMACEUTICAL, COSMETIC AND/OR FOOD COMPOSITION WITH ANTIOXIDANT PROPERTIES

(75) Inventors: Jean-Francois Rees, Hevillers; Marléne Dubuisson, Geer; André Trouet, Herent, all of (BE)

(73) Assignee: Universite Catholique de Louvain, Lovain-la-Neuve (BE)

( * ) Notice: Subject to any disclaimer, the term of this patent is extended or adjusted under 35 U.S.C. 154(b) by 0 days.

(21) Appl. No.: 09/402,099

(22) PCT Filed: Mar. 30, 1998

(86) PCT No.: PCT/BE98/00044

§ 371 Date: Feb. 14, 2000

§ 102(e) Date: Feb. 14, 2000

(87) PCT Pub. No.: WO98/43641

PCT Pub. Date: Oct. 8, 1998

(30) Foreign Application Priority Data

Mar. 28, 1997 (BE) .............................................. 9700294

(51) Int. Cl.$^7$ ............................................ A61K 31/495
(52) U.S. Cl. ....................................................... 514/255
(58) Field of Search ......................................... 514/255

(56) References Cited

FOREIGN PATENT DOCUMENTS

| CA | 2215046 | 3/1996 |
|---|---|---|
| WO | 96/28160 | 9/1996 |

OTHER PUBLICATIONS

Chen et al. Chem. Lett. (1993), 2 pages 287–290 ISSN: 0366–7022.*
Lucas et al., Anal. Biochem, vol. 206, 1992, pp. 273–277.
Inoue et al., Chem. Lett., vol. 3, 1980, pp. 299–300.
Nakano, Determination of Superoxide Radical ans Singlet Oxygen Based on Chemiluminescence of Luciferin Analogs, Methods in Enzymology, vol. 186, pp. 585–591.

* cited by examiner

Primary Examiner—Theodore J. Criares
Assistant Examiner—Jennifer Kim
(74) Attorney, Agent, or Firm—Knobbe, Martens, Olson & Bear LLP

(57) ABSTRACT

A pharmaceutical, cosmetic, and/or food composition containing a pyrazine derivative useful for preparing a medicament for preventing and/or treating pathologies related to the activity of oxygen promoters or for treating cancer tumors. The pathologies which can be treated include inflammatory diseases, carcinogenic diseases, atherosclerosis, or cancerous tumors. The pyrazine may be coelenteramine or its derivatives.

14 Claims, 6 Drawing Sheets

PHARMACEUTICAL, COSMETIC AND/OR FOOD COMPOSITION WITH ANTIOXIDANT PROPERTIES

This is the U.S. national phase under 35 U.S.C. §371 of International Application PCT/BE98/00044, filed Mar. 30, 1998.

OBJECT OF THE INVENTION

The present invention relates to a pharmaceutical, cosmetic and/or foodstuff composition intended in particular for the prevention and/or treatment of diseases associated with pro-oxidizing agents.

The present invention also relates to the use of the pharmaceutical, cosmetic and/or foodstuff composition according to the invention.

TECHNOLOGICAL BACKGROUND AND PRIOR ART

Patent Application WO96/28160 describes a pharmaceutical, cosmetic and/or foodstuff composition having antioxidizing properties and comprising a pyrazine derivative or a precursor thereof, the derivatives being imidazolopyrazines, such as coelenterazine.

This document also describes the use of such a pharmaceutical, cosmetic and/or foodstuff composition for treatment of diseases associated with the action of pro-oxidizing agents, such as inflammatory diseases, or the use of the said composition for treatment of cancerous tumours.

Antioxidizing molecules, such as vitamins, such as vitamin E (soluble in lipids), or cysteine derivatives (soluble in water) have also already been used in cosmetic, pharmaceutical and/or foodstuff applications. However, such antioxidizing molecules are characterized either by a low solubility in water or by a high toxicity, by too low an efficacy or by a low stability with respect to oxygen.

OBJECT OF THE INVENTION

The object of the present invention is to obtain a pharmaceutical, cosmetic and/or foodstuff composition which allows bonding of pro-oxidizing agents and should not have the disadvantages of the prior art.

A particular object of the present invention is to obtain a pharmaceutical, cosmetic and/or foodstuff composition advantageously allowing the prevention and/or treatment of diseases associated with pro-oxidizing agents.

Another object of the present invention is to provide a pharmaceutical, cosmetic and/or foodstuff composition which is characterized by an improved stability with respect to products of the prior art, by a low toxicity or an absence of toxicity, and by a significant solubility in a large number of solvents and/or lipids.

Characteristic Elements of the Present Invention

The present invention relates to a pharmaceutical, cosmetic and/or foodstuff composition comprising a pyrazine derivative of the formula

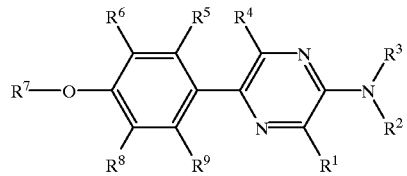

in which the radicals $R^1$ to $R^9$ are H, radicals chosen from the group consisting of alkyl, alkenyl, alkinyl, aryl, arylalkyl, alkylaryl, heteroaryl, heteroalkyl and hetero-(alkylaryl and arylalkyl), preferably having 1 to 20 carbon atoms and optionally containing 1 to 10 heteroatoms, the carbon atoms of which can optionally be substituted by any element of the Mendeleev table, preferably an element chosen from the group consisting of H, B, N, O, F, P, S, Cl, As, Se, Br, Te and I, or chains of the formula $(R^5 \times R^6)_n$, where $n \geq 1$, x represents one or more heteroatoms and $R^5$ and $R^6$ are radicals chosen from the group consisting of alkyl, alkenyl, alkinyl, aryl, arylalkyl, alkylaryl, heteroaryl, heteroalkyl and hetero-(alkylaryl and arylalkyl) having 1 to 20 carbon atoms and optionally containing 1 to 10 heteroatoms, the carbon atoms of which can optionally be substituted by any element of the Mendeleev table, preferably an element chosen from the group consisting of H, B, N, O, F, P, S, Cl, As, Se, Br, Te and I; and optionally a suitable pharmaceutical, cosmetic and/or foodstuff vehicle.

Preferably, in the pyrazine derivative according to the invention, the radicals $R^2$ to $R^9$ are H and the radical $R^1$ is a radical of the formula

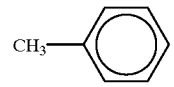

and optionally a suitable pharmaceutical, cosmetic and/or foodstuff vehicle.

Another aspect of the present invention relates to the use of the composition according to the invention for bonding pro-oxidizing agents (activated forms of oxygen), such as peroxides, superoxides etc.

The present invention also relates to a process for bonding pro-oxidizing agents in which the pharmaceutical, cosmetic and/or foodstuff composition is brought into contact with the said pro-oxidizing agents.

The present invention also relates to a process for treatment and/or prevention of diseases associated with the action of pro-oxidizing agents, in particular inflammatory diseases, and a process for treatment and/or prevention of atherosclerosis, in which the pharmaceutical, cosmetic and/or foodstuff composition according to the present invention is administered to a patient (human or animal).

In the said processes, the pharmaceutical, cosmetic and/or foodstuff composition is combined with a therapeutic effect. However, the said composition can also be characterized as being a "functional" foodstuff composition.

A "functional foodstuff composition" is characterized in that it comprises one or more ingredients which are capable of having a beneficial physiological effect on the consumer, such as the prevention of an illness, the treatment of an illness or the activation of biorhythm or the immune system. Such a functional foodstuff composition can be incorporated into the normal diet of the consumer such that a general improvement in the health of the patient is obtained, or to obtain treatment or prevention of a particular illness, in as much as the said functional foodstuff composition has a significant effect on the consumer from both the preventive and the therapeutic point of view.

The said pharmaceutical, cosmetic and/or foodstuff composition will comprise a sufficient amount of the pyrazine derivative according to the invention to obtain a prevention or a significant therapeutic effect on the consumer.

The proportion of pyrazine derivative according to the invention in the pharmaceutical, cosmetic and/or foodstuff composition according to the invention will vary as a function of the daily amounts of the product absorbed, in accordance with suitable foodstuffs, cosmetics and pharmaceuticals legislation, sensory considerations and the secondary effects which may exist with the derivatives according to the invention and/or their pharmaceutical, cosmetic and/or foodstuff vehicles used.

The pharmaceutical, cosmetic and/or foodstuff vehicles of the compositions according to the invention are suitable vehicles in particular for oral administration, for example in the form of coated or non-coated tablets, pills, capsules, solutions, essential oils and/or syrups.

Other suitable pharmaceutical, cosmetic and/or foodstuff vehicles can be used, depending on the mode of administration chosen.

In particular, these pharmaceutical, cosmetic and/or foodstuff vehicles can be sun creams or oils well-known to the person skilled in the art, which may be smeared over various areas of the human or animal body in combination with other skin-protection agents.

In addition, the products of the invention can easily be incorporated into solvents (aqueous media, alcohols etc.) or lipids (for example in combination with foodstuff oils or sun-tanning oils).

The pharmaceutical, cosmetic and/or foodstuff compositions according to the invention are prepared by processes generally used by the person skilled in the art, in particular by pharmacists, and can comprise any pharmaceutically suitable, solid or liquid non-toxic vehicle or additive.

Incorporation of the derivatives according to the invention into a galenical medium may also be envisaged.

The percentage of active product (pyrazine derivative) in the pharmaceutical, cosmetic and/or foodstuff vehicle can vary within very wide ranges, which are generally limited by the tolerance and the level of acceptance of the composition by the consumer.

The limits are generally determined by the frequency of consumption of the composition by the consumer.

A last aspect of the present invention relates to the use of the composition according to the invention for the preparation of a medicament intended for prevention and/or treatment of diseases associated with the action of pro-oxidizing agents.

In particular, the present invention relates to the use of the composition according to the invention for the preparation of a medicament intended for prevention and/or treatment of inflammatory or carcinogenic diseases, prevention of atherosclerosis and/or treatment of cancerous tumours.

EXAMPLES

Coelenteramine (CLM) is a naturally occurring product present in marine organisms which is derived from the oxidation of coelenterazine.

The structure of coelenteramine is illustrated below. This structure shows the following characteristics:

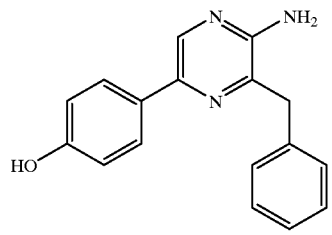

Example 1

Stability

Coelenteramine is characterized by an excellent stability towards oxygen, both in the form of a powder and after solubilization in aqueous and organic solvents. In fact, this molecule is not changed by remaining in an aqueous solvent exposed to air for several days. After several days, no degradation product of coelenteramine was identified by HPLC and TLC chromatographic analysis.

Example 2

Toxicity

Figure 1:
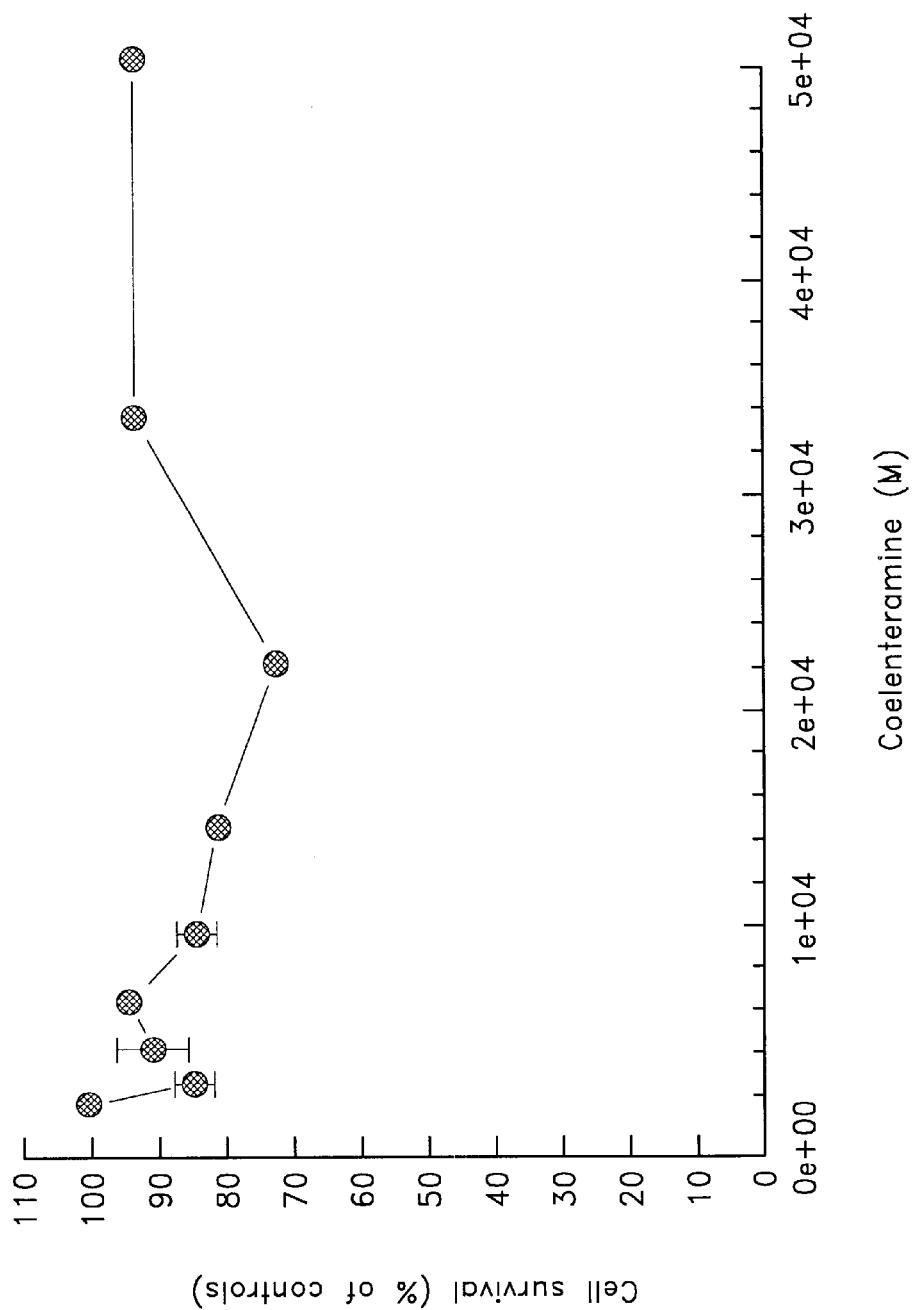
FIG. 1 shows the percentage cell survival of rat hepatocytes as a function of increasing (molar) doses of coelenteramine.

Coelenteramine is characterized by an absence of toxicity both on hepatic cells and on intestinal cells or fibroblasts. Coetenteramine was applied to primary cultures of rat hepatocytes cultured in microplates (20,000 cells per well, 200 μl). The doses of CLM ranged from $1.3 \times 10^{-5}$ to $5 \times 10^{-4}$ M. After a period of 24 hours, their survival was evaluated by measuring the contents of total proteins in each well (Bradford method). The results, shown on FIG. 1, expressed in percentage survival of controls not treated with CLM, show that the latter is not at all toxic to the hepatocytes at these concentrations. Similar results were obtained on human fibroblasts (MRC-5) and human intestinal cells (CACO2).

Example 3

Protective Activity of Lipoproteins

Atherosclerosis constitutes a major cause of cardiovascular mortality. Epidemiological studies have shown that an accelerated development of atherosclerosis is associated with a high plasma level of "low-density lipoproteins" (LDL). It is known that LDL contain various antioxidizing agents, the major element of which is α-tocopherol (vitamin E). Ascorbic acid (vitamin C), ubiquinone and β-carotene represent the other main antioxidizing molecules of LDL. It has been demonstrated in vitro that the conversion of macrophages into spumous cells charged with lipids (which are the main constituents of the atherosclerosis plaque) is associated with a change in LDL of an oxidative nature. The oxidation of LDL is a process mediated by free radicals and initiated by peroxidation of polyunsaturated fatty acids after consumption of antioxidizing agents. The oxidation of LDL greatly increases atherogenic properties. Epidemiological studies have shown an inverse relationship between cardiovascular mortality and the plasma concentration of antioxidants (such as vitamin E). Consequently, water- and liposoluble antioxidants can protect LDL and delay or prevent their oxidation process. Thus, in order to estimate the protective effect of coelenteramine against atherosclerosis, the in vitro oxidation of LDL in the absence or in the presence of varying concentrations of coelenteramine is compared.

Oxidation of the polyunsaturated fatty acids of LDL is accompanied by the formation of joint dienes, which have a maximum absorbance at 234 nm. These joint dienes result from rearrangement of the double bonds of polyunsaturated fatty acids following removal of a malonic hydrogen. The increase in the absorption of joint dienes can be measured directly in solution without resorting to extraction of the lipids. A latency phase during which few dienes are produced, a propagation phase during which the absorbance at 234 nm increases rapidly to reach a plateau and a decomposition phase where the aldehydes formed also absorb in the region of 210–240 nm, thus producing a new increase in the absorbance at 234 nm, are observed in succession. Measurement of the conjugated dienes currently seems to be the best indicator of the oxidizability of LDL if pure LDL preparations are available (Esterbauer et al. (1989)).

In an acellular medium, oxidation of LDL can be catalysed by metal ions, such as copper, or induced by a water-soluble free-radical initiator, such as 2,2'-azobis(2-amidinopropane) (AAPH).

To measure the joint dienes, a solution of LDL (final concentration of 50 µg protein/ml PBS buffer, pH 7.4) is incubated in the presence of 5 µM copper or 2 µM AAPH and in the absence or in the presence of varying concentrations of CLM in a quartz cell with an optical path of 1 cm. The absorbances at 234 nm of various samples are measured as a function of time on a UV-visible spectrophotometer (DU-8, Beckman). A blank is obtained by means of a phosphate solution without LDL but containing 5 µM $CuCl_2.2H_2O$ and 2.5 µM CLM. The tests are carried at 30° C. for oxidation of the LDL in the presence of copper and at 37° C. in the presence of AAPH.

Figure 2:
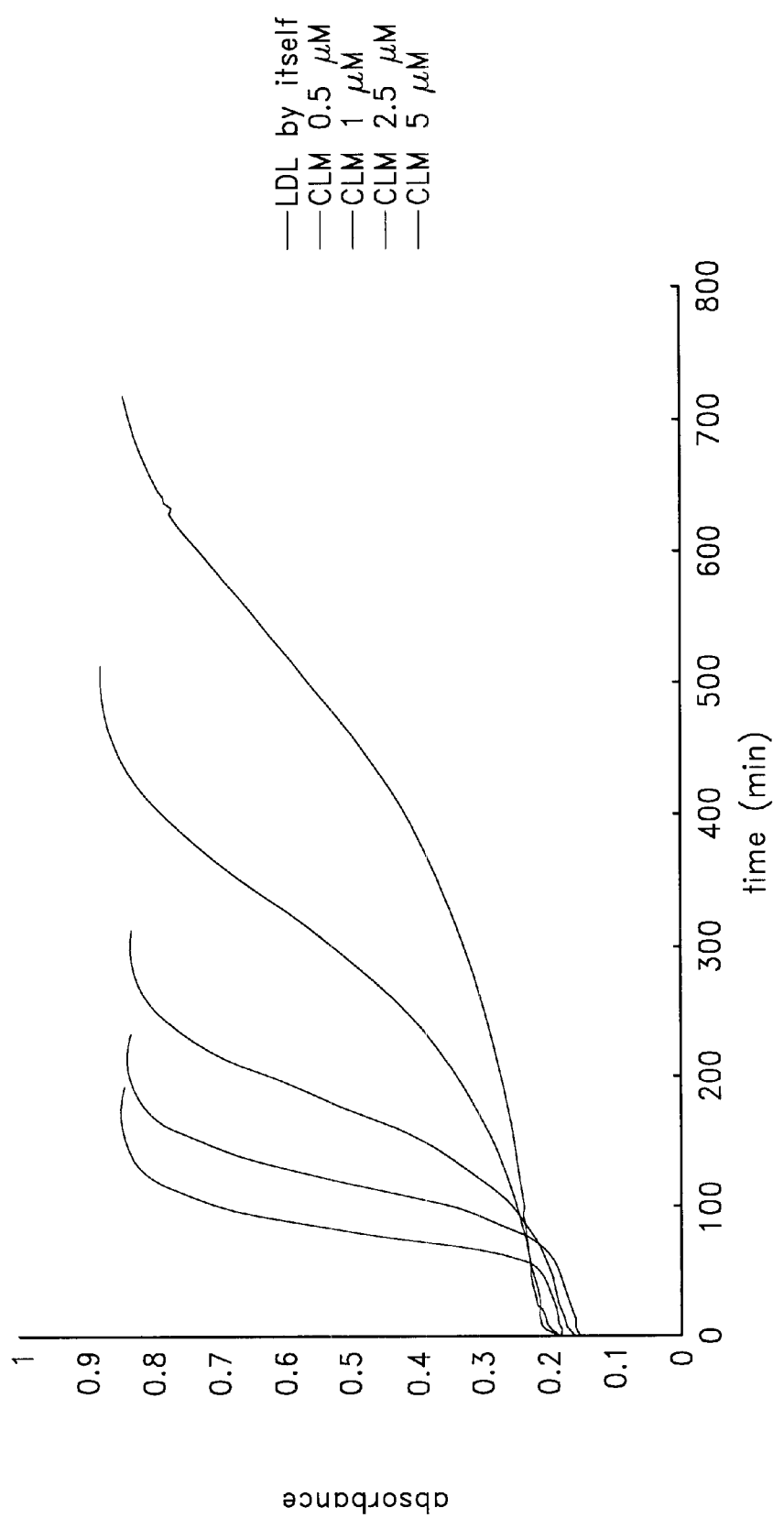
FIG. 2 shows the oxidation of "low-density lipoproteins" (LDL) with a free-radical water-soluble initiator (AAPH) in the presence of coelenteramine.
Figure 3:
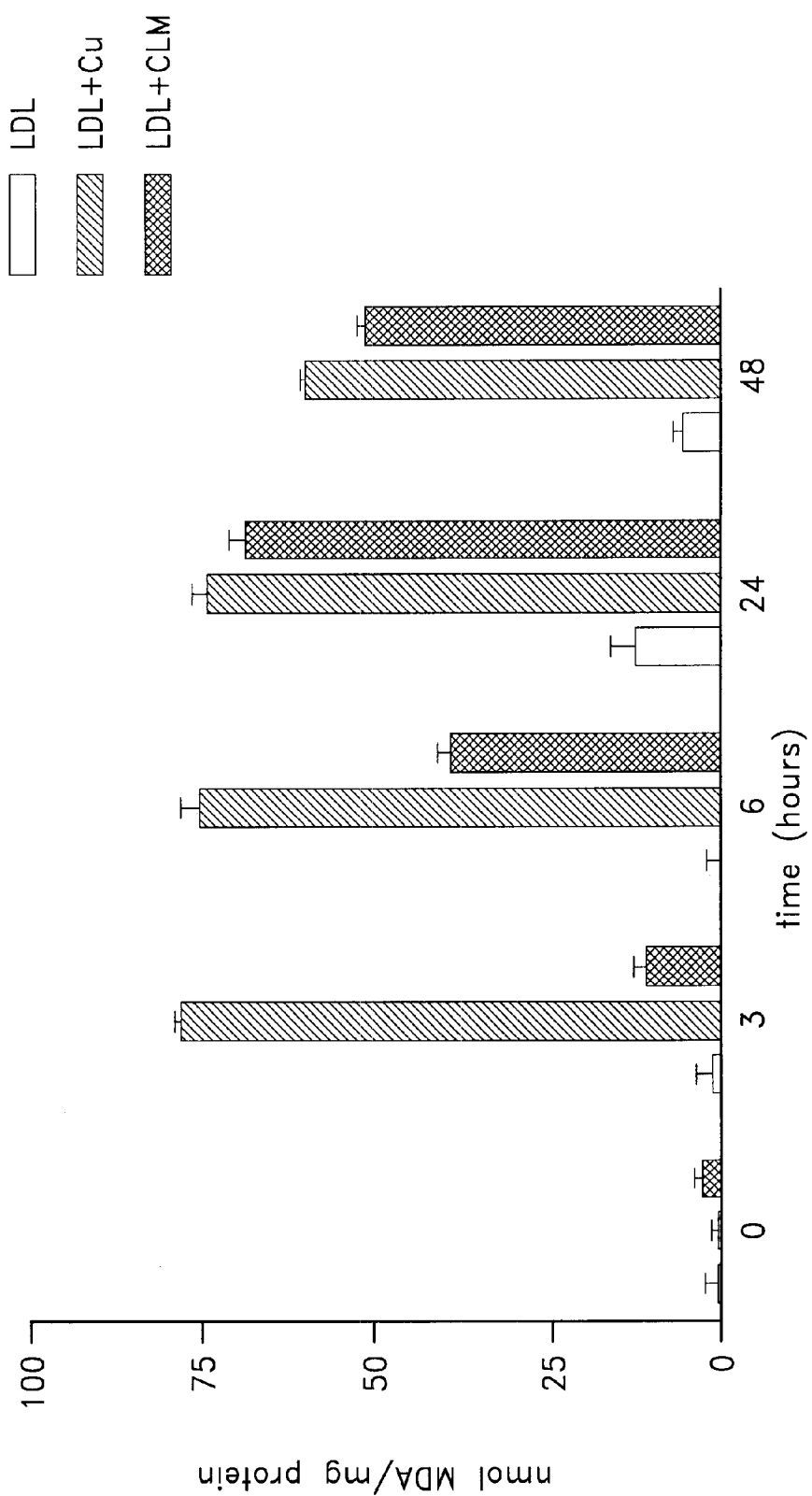
FIG. 3 shows the course of the oxidation of human "low-density lipoproteins" by $Cu^{2+}$ as a function of time.

The results indicate that CLM has a significant protective action on the LDL with respect to their oxidation by AAPH or copper. The action of CLM on the oxidation of LDL by AAPH is illustrated in FIG. 2, in which the significant slowing down in the appearance of joint dienes with increasing concentrations of CLM is seen. Similar results are found if the oxidation of the LDL is realized with copper. FIG. 3 illustrates the delay in the appearance of TBARS (thiobarbituric acid reactive substances), essentially corresponding to malonaldialdehyde (MDA), a product of the oxidation of the lipids contained in LDL.

Example 4
Protective Action on Cells Subjected to an Oxidative Stress

Primary cultures of hepatocytes were subjected to the action of tert-butyl hydroperoxide (t-BHP) and nitrofurantoin (NF). The action of t-BHF is associated with its direct oxidizing power, while the action of NF results from the production of superoxide anions during its metabolization by the cytochrome P450 of cells.

Figure 4:
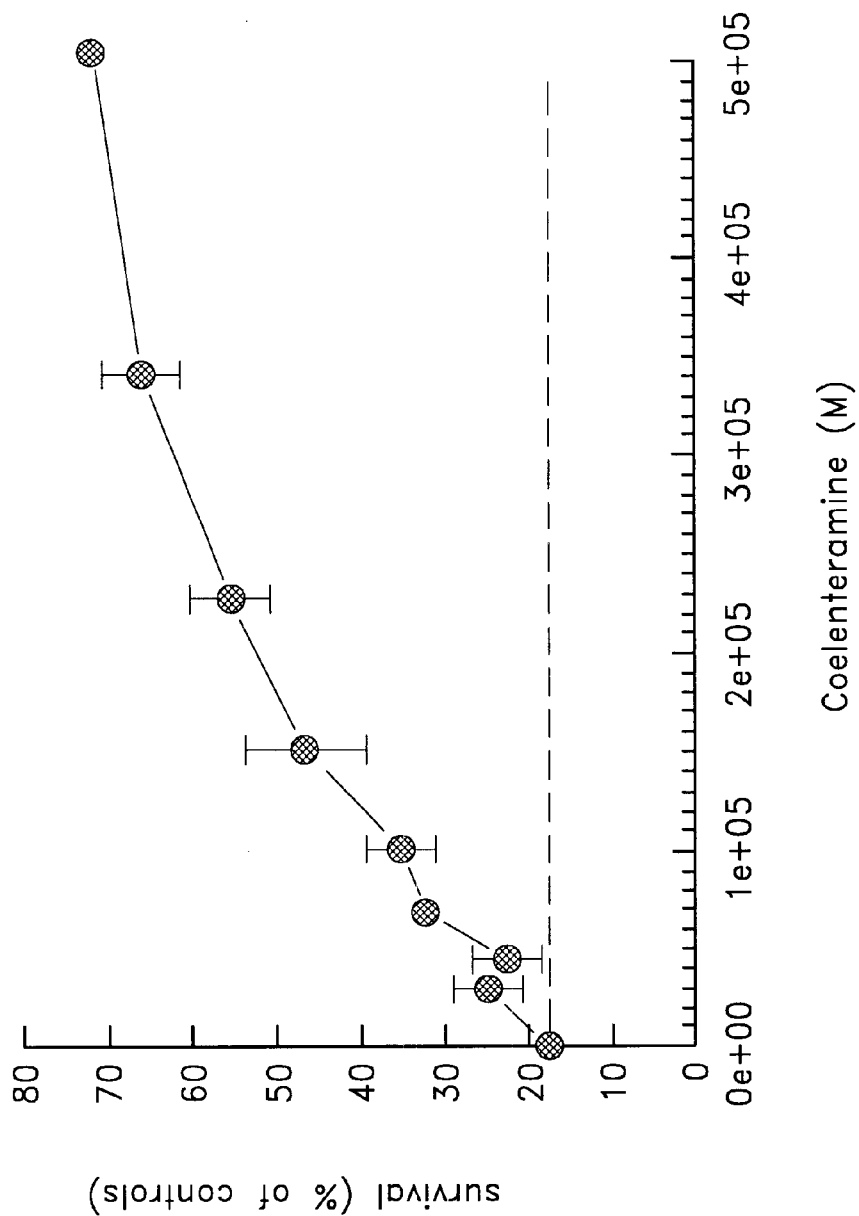
FIG. 4 illustrates the percentage survival of hepatocytes subjected to the action of nitrofurantoin.

FIG. 4 illustrates the survival of hepatocytes subjected to the action of $3 \times 10^{-4}$ M NF for 6 hours. At the end of this treatment, the survival (estimated by the MTT method) was 18% in the control groups. If CLM is added to the culture medium, the survival of the hepatocytes increases regularly, to reach 70% of the controls at $5 \times 10^{-5}$ M CLM.

Figure 5:
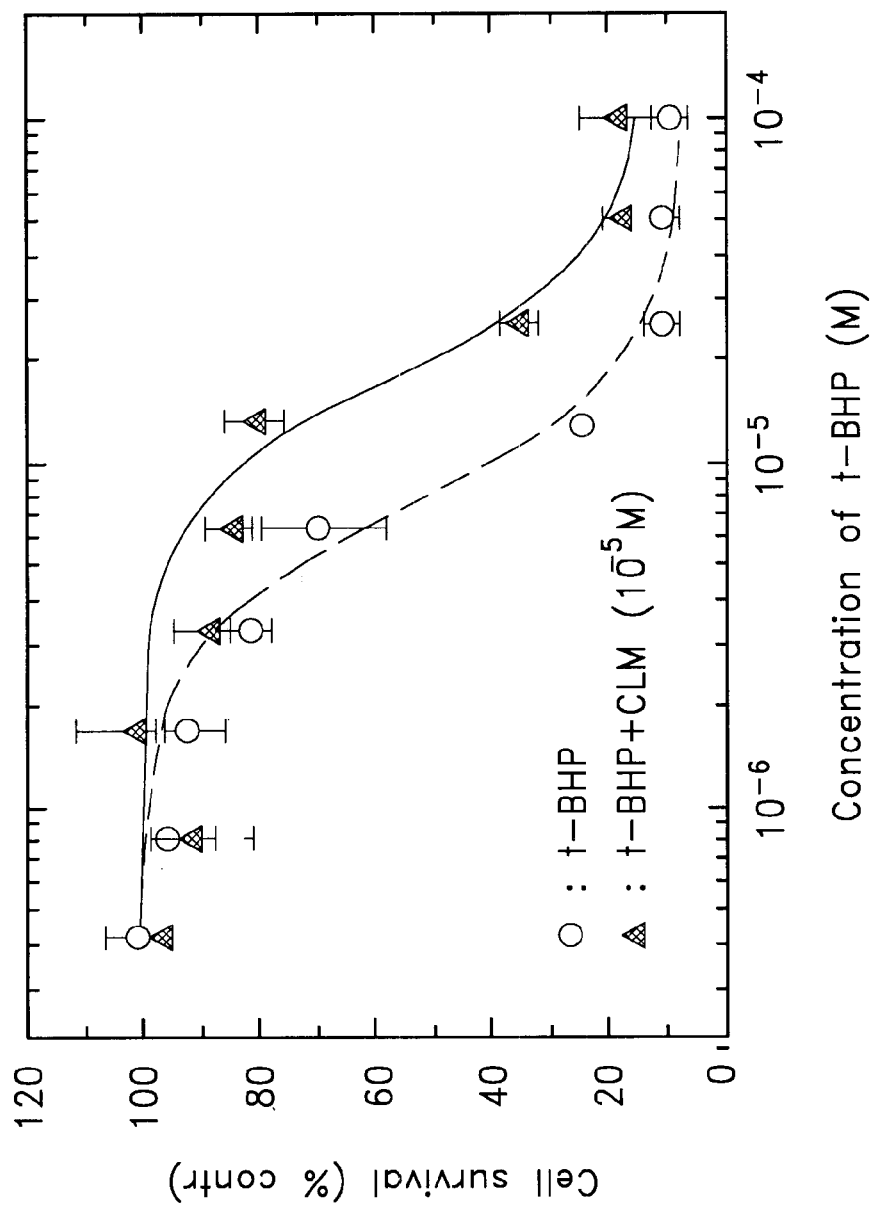
FIG. 5 illustrates the increase in the resistance of fibroblasts subjected to the action of an oxidative stress (increasing concentration of t-BHP) in the presence or in the absence of coelenteramine.

FIG. 5 illustrates the increase in the resistance of fibroblasts subjected to the action of t-BHP by means of $10^{-5}$ M CLM. In this case, a significant displacement of the cytotoxicity curve (measured by the MTT test) of t-BHP towards higher concentrations in the presence of CLM is observed.

Figure 6:
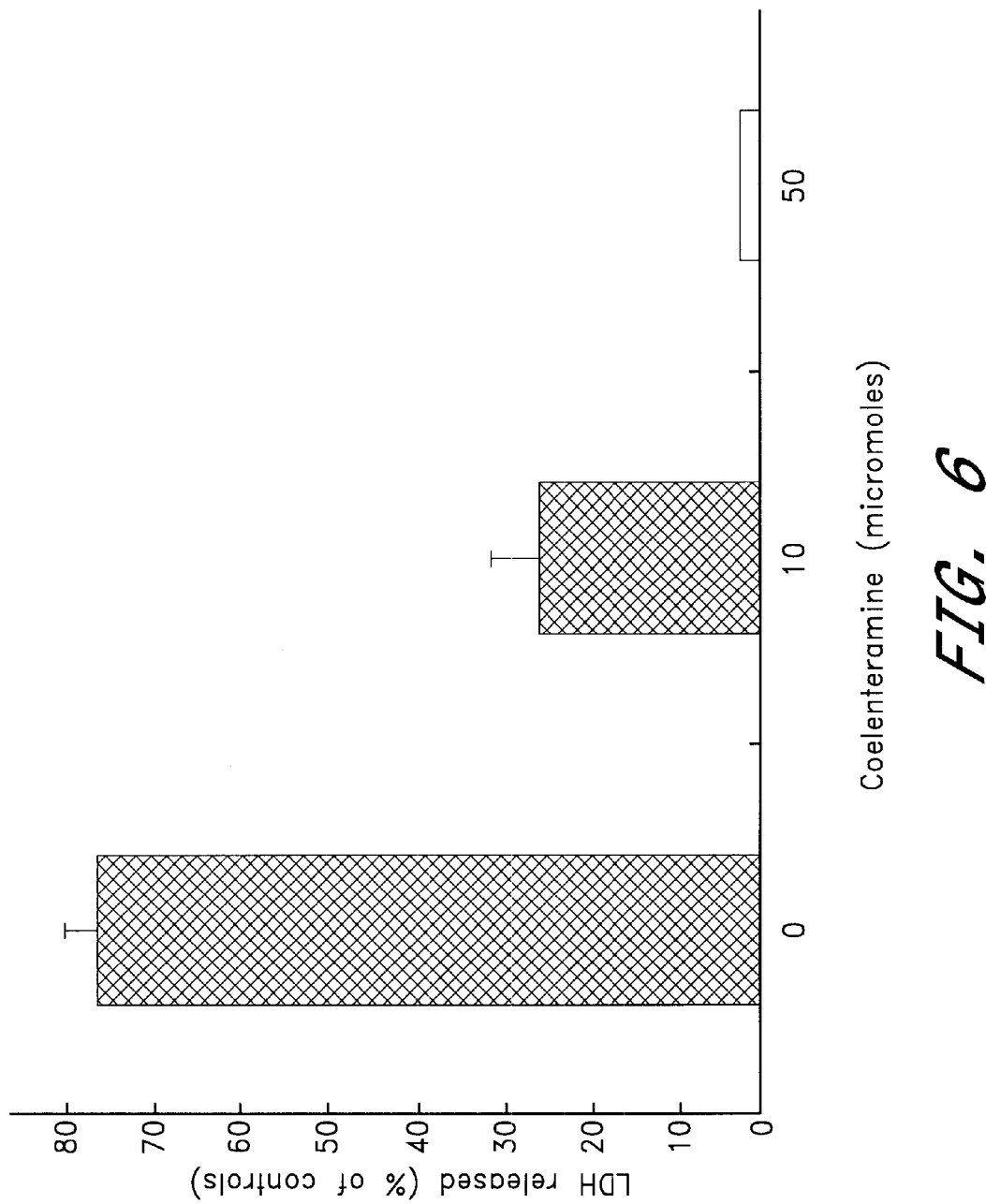
FIG. 6 illustrates the reduction in the release of lactate dehydrogenase by rat hepatocytes when increasing doses of coelenteramine are added to the culture medium.

Similar results were observed in hepatocytes treated with t-BHP. FIG. 6 illustrates the reduction in the release of lactate dehydrogenase (LDH), a cytotoxicity indicator, by cells if CLM (10 and 50 µM) is added to the culture medium. The mortality, which is 75% in the controls, reaches only a few % in the presence of 50 µM CLM.

What is claimed is:

1. A pharmaceutical, cosmetic and/or foodstuff composition comprising in a carrier selected from the group consisting of pharmaceutical, cosmetic, and or foodstuff a pyrazine derivative of the formula

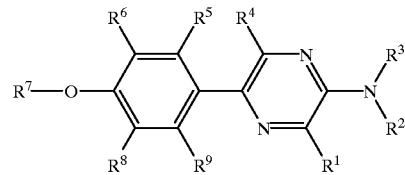

wherein the radicals $R^1$ to $R^9$ are selected from the group consisting of H, radicals or substituted radicals selected from the group consisting of alkyl, alkenyl, alkinyl, aryl, arylalkyl, alkylaryl, heteroaryl, heteroalkyl, and hetero-(alkylaryl and arylalkyl), and chains of the formula ($R^5$ x $R^6)_n$, where n≧1, x represents one or more heteroatoms, and $R^5$ and $R^6$ are radicals or substituted radicals selected from the group consisting of alkyl, alkenyl, alkinyl, aryl, arylalkyl, alkylaryl, heteroaryl, heteroalkyl and hetero-(alkylaryl and arylalkyl).

2. The pharmaceutical, cosmetic and/or foodstuff composition according to claim 1, wherein the radicals $R^2$ to $R^9$ are H, and the radical $R^1$ is a radical of the formula

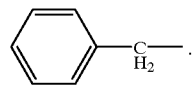

3. A method for bonding pro-oxidizing agents, comprising contacting the pharmaceutical, cosmetic and/or foodstuff composition according to claim 1 with said pro-oxidizing agents.

4. A method for prevention and/or treatment of diseases associated with the action of pro-oxidizing agents, comprising:
preparing a medicament comprising the pharmaceutical composition according to claim 1; and
administering an effective amount of said medicament to a subject in need of treatment.

5. A method for prevention and/or treatment of inflammatory diseases comprising:
preparing a medicament comprising the pharmaceutical composition according to claim 1; and
administering an effective amount of said medicament to a subject in need of treatment.

6. A method for the prevention and/or treatment of carcinogenic diseases comprising:
preparing a medicament comprising the pharmaceutical composition according to claim 1; and
administering an effective amount of said medicament to a subject in need of treatment.

7. A method for prevention and/or treatment of atherosclerosis comprising:
preparing a medicament comprising the pharmaceutical composition according to claim 1; and
administering an effective amount of said medicament to a subject in need of treatment.

8. A method for treatment of cancerous tumors comprising:
preparing a medicament comprising the pharmaceutical composition according to claim 1; and
administering an effective amount of said medicament to a subject in need of treatment.

9. A method for bonding pro-oxidizing agents, comprising contacting the pharmaceutical, cosmetic and/or foodstuff composition according to claim 2 with said pro-oxidizing agents.

10. A method for prevention and/or treatment of diseases associated with the action of pro-oxidizing agents, comprising:
preparing a medicament comprising the pharmaceutical composition according to claim 2; and
administering an effective amount of said medicament to a subject in need of treatment.

11. A method for prevention and/or treatment of inflammatory diseases comprising:
preparing a medicament comprising the pharmaceutical composition according to claim 2; and
administering an effective amount of said medicament to a subject in need of treatment.

12. A method for the prevention and/or treatment of carcinogenic diseases comprising:
preparing a medicament comprising the pharmaceutical composition according to claim 2; and
administering an effective amount of said medicament to a subject in need of treatment.

13. A method for prevention and/or treatment of atherosclerosis comprising:
preparing a medicament comprising the pharmaceutical composition according to claim 2; and
administering an effective amount of said medicament to a subject in need of treatment.

14. A method for treatment of cancerous tumors comprising:
preparing a medicament comprising the pharmaceutical composition according to claim 2; and
administering an effective amount of said medicament to a subject in need of treatment.

* * * * *